(12) United States Patent
Bergmann et al.

(10) Patent No.: US 8,383,332 B2
(45) Date of Patent: Feb. 26, 2013

(54) PROCALCITONIN FOR THE DIAGNOSIS OF BACTERIAL INFECTIONS AND GUIDANCE OF ANTIBIOTIC TREATMENT IN PATIENTS WITH ACUTE STROKE OR TRANSIENT ISCHEMIC ATTACK

(75) Inventors: Andreas Bergmann, Berlin (DE); Oliver Hartmann, Berlin (DE); Frauke Hein, Berlin (DE); Beat Müller, Basel (CH)

(73) Assignee: B.R.A.H.M.S. GmbH, Henningsdorf (DE)

( * ) Notice: Subject to any disclaimer, the term of this patent is extended or adjusted under 35 U.S.C. 154(b) by 189 days.

(21) Appl. No.: 12/902,533

(22) Filed: Oct. 12, 2010

(65) Prior Publication Data

US 2011/0086831 A1    Apr. 14, 2011

(30) Foreign Application Priority Data

Oct. 13, 2009    (EP) ..................... 09012947

(51) Int. Cl.
  *C12Q 1/00*    (2006.01)
  *G01N 33/53*    (2006.01)
(52) U.S. Cl. ............................................ 435/4; 435/7.1
(58) Field of Classification Search ........................ None
  See application file for complete search history.

(56) References Cited

PUBLICATIONS

Miyakis et al (Clinica Chimica Acta vol. 350, pp. 237-239, 2004).*
Morgenthaler et al (Clin. Lab. vol. 48, pp. 263-270, 2002).*

* cited by examiner

*Primary Examiner* — Albert Navarro
(74) *Attorney, Agent, or Firm* — Millen, White, Zelano, Branigan, P.C.

(57) ABSTRACT

The present invention relates to an in vitro method for the diagnosis and treatment guidance of a bacterial infection in patients suffering from an acute ischemic or hemorrhagic stroke, comprising the determination of the level of Procalcitonin (PCT) or a fragment thereof having at least 12 amino acid residues in a sample of a bodily fluid from said patient and the correlation of the determined level to the diagnosis of a bacterial infection in said patient.

21 Claims, 2 Drawing Sheets

PROCALCITONIN FOR THE DIAGNOSIS OF BACTERIAL INFECTIONS AND GUIDANCE OF ANTIBIOTIC TREATMENT IN PATIENTS WITH ACUTE STROKE OR TRANSIENT ISCHEMIC ATTACK

FIELD OF THE INVENTION

The invention is in the field of clinical diagnostics. Particularly, the invention relates to the determination of the level of Procalcitonin (PCT) in a sample derived from a bodily fluid of a subject after an acute stroke or a transient ischemic attack.

BACKGROUND OF THE INVENTION

Stroke is defined as an acute focal neurological deficit resulting from a cerebrovascular disease. The two main types of stroke are ischemic and hemorrhagic, accounting for approximately 85% and 15%, respectively (Hickey 2003. The clinical practice of neurological and neurosurgical nursing (5th ed.). Philadelphia: Lippincott, Williams & Wilkins). When an ischemic stroke occurs, the blood supply to the brain is interrupted and brain cells are deprived of glucose and oxygen. Approximately 45% of ischemic strokes are caused by small or large artery thrombus, 20% are embolic origin, and others have an unknown cause (Hickey 2003. The clinical practice of neurological and neurosurgical nursing (5th ed.). Philadelphia: Lippincott, Williams & Wilkins).

Transient ischemic attack (TIA) (also known as "mini-stroke") is defined on tissue-based characteristics as a transient episode of neurological dysfunction caused by focal brain, spinal cord or retinal ischemia, without acute infarction (Easton et al. 2009. Stroke 40: 2276-93). TIA is further characterized by a sudden onset of neurological symptoms that resolve completely within 24 hours. TIA may be reported in 0.5% to 8% of the elderly population (Bots et al., 1997. Stroke 28(4): 768-73). A patient with a TIA is at high risk of subsequent adverse events. The 90-day risk of stroke has been reported to be greater than 10%, with the highest risk occurring within the first 2 days (Johnston et al., 2003. Neurology 60: 1429-34).

Stroke is one of the most important vascular diseases. Stroke remains the second leading cause of death worldwide and is one of the main causes of adult disability and early invalidity in Europe (Murray and Lopez, 1997. Lancet 349: 1269-76; Murray and Lopez 1997. Lancet 349:1498-504). In the US, more than 700 000 people have a stroke each year whereof 550,000 are first strokes (Thom et al. 2006. Circulation 113: 85-151). Therefore, it is an important public health problem and a burden to health care providers and to the community at large because of the amount of effort that has to be invested in the planning and provision of health care.

The incidence of stroke increases markedly with increasing age in our society (Madan and Wagener, 1992. Stroke 23:1230-36). Most ischemic strokes occur between the ages of 71 and 80 years while most hemorrhagic strokes appear between 60 and 70 years (Colombo et al., 1989. Rivista de Neurologia 59: 1-7).

Prognosis of the outcome for stroke patients after a defined interval can either be functional or related to individual survival. For functional outcome prognosis, the morbidity of a patient after a defined time is determined using a score system such as the "modified Ranking Scale" (mRS; Bonita and Beaglehole, 1988. Stroke 19: 1497-1500) or the "National Institutes of Health Stroke Scale" (NIHSS; Adams et al., 1999. Neurology 53: 126-31). The NIHSS is currently considered the "gold standard". The functional outcome may also be expressed in terms of need of nursing care or with respect to activities of daily living (ADL), e.g. according to the Barthel Index and Ranking Scale (Collin et al., 1988. International Disability Study 10: 61-3; Bonita and Beaglehole, 1988. Stroke 19: 1497-1500).

The prognosis of stroke mainly depends on the incidence of complications (Davenport et al. 1996. Stroke 27: 415-20; Johnston et al. 1998. Stroke 29: 447-53). Infections, especially pneumonias, are the third most common stroke complication (Langhorne et al. 2000. Stroke 31: 1223-9; Katzan et al. 2003. Neurology 60: 620-5) and thought to be the most common cause of poor outcome and death in stroke patients (Henon et al. 1995. Stroke 26: 392-8; Hilker et al. 2003. Stroke 34: 975-81; Heuschmann et al. 2004. Arch Intern Med 164: 1761-8). The frequency of infections in acute stroke patients is very high: 21-65% of patients with an acute stroke develop infections and 10-22% develop pneumonias (Castillo et al. 1998. Stroke 29: 2455-60; Davenport et al. 1996. Stroke 27: 415-20; Georgilis et al. 1999. J Int Med 246: 203-9; Grau et al. 1999. J Neurol Sci 171: 115-20; Johnston et al. 1998. Stroke 29: 447-53; Langhorne et al. 2000. Stroke 31: 1223-9), compared to the incidence of nosocomial or healthcare associated infections occurring in an average of 7-10% of all patients (Bucher et al. 2000. Tidsskr Nor Laegeforen 120: 472-5) and about 3% in postoperative patients (Smyth and Emmerson 2000. J Hasp Infect 45: 173-84). It was shown that the risk of infection is highest in the acute state of stroke at the first and second day after stroke (Grau et al. 1999. J Neural Sci 171: 115-20; Kong et al. 1998. Arch Phys Med Rehabil 79: 1535-9). The high incidence of infections in stroke patients is likely to be the result of an impaired immune function (Livingston et al. 1988. Arch Surg 123: 1309-12; Woiciechowsky et al. 1998. Nat Med 4: 808-13; Dirnagl et al. 2007. Stroke 38: 770-3). Immunodepression after stroke can be detected within a few hours after induction of ischemia and may last for several weeks (Dirnagl et al. 2007. Stroke 38: 770-3). Several risk factors contribute to the increased susceptibility of stroke patients for infections: aspiration due to drowsiness, impaired bulbar reflexes, dysphagia, and hypostasis in bed-ridden patients, as well as the need for invasive medical procedures (Perry and Love 2001. Dysphagia 16: 7-18).

Post-stroke infection can also affect patients with TIA and is most likely, such as acute ischemic and hemorrhagic stroke, associated with a poor short-term outcome (Kwan and Hand 2007. Acta Neural Scand 115:331-8).

It is well known that stroke produces an inflammatory response with an increase of white blood cell (WBC) count in peripheral blood (Kazmierski et al. 2001. Wiad Lek 54:143-51) as well as body core temperature (Boysen and Christensen 2001. Stroke 32:413-7), brain temperature (Schwab et al. 1997. Neurology 48:762-7) and C-reactive protein (CRP) (Idicula et al. 2009. BMC Neurology 9:18). However, the systemic inflammatory response after stroke may rather result from a response to the necrotic tissue itself than from an infection. Necrotic tissue is eliminated by cellular, humoral, and metabolic mechanisms, which are all part of the inflammatory reaction (Kogure et al. 1996. Acta Neurochir Suppl (Wien) 66:40-3). The increase in body temperature starts within 24 hours of the event, whereas fever due to infection seems to have a later onset (Boysen and Christensen 2001. Stroke 32:413-7; Davalos et al. 1997. Cerebrovasc Dis 7:64-9; Castillo et al. 1999. Cerebrovasc Dis 9:22-7; Castillo et al. 1998. Stroke 29:2455-60). In ischemic stroke patients without evidence of infection, the elevation of body temperature and WBC as well as CRP was significantly correlated with lesion volume and initial stroke severity (Audebert et al. 2004. Stroke 35: 2128-2133). Moreover, the systemic inflammatory response was shown to be attenuated by a successful thrombolysis therapy. Thus, the induced rescue of brain tissue may be a result of reduced systemic inflammation by avoiding cerebral necrosis.

Procalcitonin (PCT) has become a well-established biomarker for the diagnosis of sepsis. PCT reflects the severity of a bacterial infection and is in particular used to monitor progression of infection into sepsis, severe sepsis, or septic shock. It is possible to use PCT to measure the activity of the systemic inflammatory response, to control success of therapy, and to estimate prognosis (Assicot et al. 1993. Lancet 341:515-8; Clec'h C et al. 2004. Crit. Care Med 32:1166-9; Lee et al. 2004. Yonsei Med J 45:29-37; Meisner et al. 2005, Curr Opin Crit. Care 11:473-480; Wunder et al. 2004. Inflamm Res 53: 158-163). The increase of PCT levels in patients with sepsis correlates with mortality (Oberhoffer et al. 1999. Clin Chem Lab Med 37:363-368).

PCT has already been used for therapy guidance of antibiotics, but not after an acute stoke. In patients representing at the emergency department with symptoms of lower respiratory tract infections, PCT was measured and only patients with PCT concentrations>0.25 ng/mL or >0.5 ng/mL were treated with antibiotics (Christ-Crain et al. 2004. Lancet 363: 600-7). In patients with community-acquired pneumonia (CAP) antibiotic treatment was based on serum PCT concentrations (strongly discouraged at PCT concentrations<0.1 ng/mL; discouraged at PCT concentrations<0.25 ng/mL; encouraged at PCT concentrations>0.25 ng/mL, and strongly encouraged at PCT concentrations>0.5 ng/mL) (Christ-Crain et al. 2006. Am J Resp Crit. Care Med 174:84-93). PCT guidance substantially reduced antibiotic use in CAP without deterioration of patients outcome. Similarly, PCT-guided therapy using the same decision thresholds as described above, also markedly reduced antibiotic use for acute respiratory tract infections in primary care without compromising patients outcome (Brief et al. 2008. Arch Intern Med 168: 2000-7).

Current guidelines on acute stroke management advise against prophylactic administration of antibiotics (Hacke et al. 2003. Cerebrovasc Dis 16: 311-37). Moreover, a randomized clinical trial of antibiotic prophylaxis recently provided evidence-based support to this recommendation, as it showed that intravenous administration of levofloxacin was not better than placebo to prevent infections in patients with acute stroke (Chamorro et al. 2005. Stroke 36: 1495-500). In contrast, in patients with acute severe stroke (mRS>3), administration of mezlocillin plus sulbactam lowered the rate of infection and may be associated with a better clinical outcome (Schwarz et al. 2008. Stroke 39: 1220-7). However, with regard to the development of possible resistance to antibiotics as well as antibiotic induced side effects, a prophylactic treatment of patients with an acute stroke is not considered to be appropriate and current guidelines on acute stroke management advise against prophylactic administration of antibiotics (Hacke et al. 2003. Cerebrovasc Dis 16: 311-37; Ringleb et al. 2008. Cerebrovasc Dis 25: 457-507).

Against the background of impaired immune function in stroke patients on the one hand and the systemic inflammatory response after stroke on the other hand, it is absolutely unclear whether PCT concentrations are changed in patients with post-stroke infections. An investigation of serum PCT levels in patients suffering from an acute stroke did not reveal significant differences between the day of hospitalization and day 7 (Miyakis et al. 2004. Clin Chim Acta 350: 437-9). No correlation of PCT levels with mortality or neurological outcome has been found in this study. Molnar and colleagues measured PCT in serum of patients with acute ischemic stroke and TIA (Molnar et al. 2008 J Clin Pathol 61: 1209-13). Although PCT was measured serially, the authors did not find any difference in PCT levels measured at different time points after stroke, except that a slight increase of PCT at 72 hours indicated subsequent post-stroke infections. The results of both studies could be attributed; to the respective PCT test systems used, namely the PCT LIA in Miyakis et al. with a functional assay sensitivity (FAS) of 0.08 ng/mL and the PCT Kryptor in Molnar et al. with a FAS of 0.06 ng/mL.

Vogelgesang et al. measured PCT values in serum of patients with stroke on days 7 and 14 after patients admission to the hospital as one out of three criteria for infection using a cut-off for PCT of >0.5 ng/mL (Vogelgesang et al. 2008. Stroke 39: 237-41).

A diagnostic method to determine the etiology of inflammatory processes by determining the concentration of PCT and to ascertain from the presence or absence of the peptide whether the inflammation is of infectious or non-infectious etiology is described in EP 0 80 702 B1.

A method for the prognosis of an outcome or assessing the risk of a patient having suffered a stroke or transient ischemic attack by determining the level of PCT is described in EP 08167512.6 and EP 08168671.9.

A method for the prognosis for a patient having a primary non-infectious disease by determining the level of PCT and correlating the PCT level to a risk of the patient to contract a further disease or medical condition which has not yet been manifested and/or is not yet symptomatic, is described in EP 07015271.5.

Regarding the high incidence of post-stroke infections and its association of a poorer outcome of stroke or TIA patients suffering a post-stroke/post-TIA infection, these patients should be closely monitored for infection.

Thus, the inventors of the present invention have investigated whether measurement of Procalcitonin levels in a sample of a bodily fluid from a patient who suffered from an acute ischemic or hemorrhagic stroke or a transient ischemic attack could be used for the diagnosis and treatment guidance of a post-stroke/post-TIA bacterial infection in these patients.

SUMMARY OF THE INVENTION

The invention relates to a method for diagnosing or identifying a bacterial infection in a patient who has suffered from an acute stroke or from a transient ischemic attack. The method comprises the following steps:
(i) providing a sample from a patient who has suffered from an acute stroke or a transient ischemic attack;
(ii) determining the level of Procalcitonin (PCT) or a fragment thereof of at least 12 amino acids in length, preferably more than 50 amino acids in length, more preferably more than 110 amino acids in length, in said sample using a PCT detection assay with a functional assay sensitivity of below 0.06 ng/mL, more preferred 0.04 ng/mL or below, even more preferred 0.03 ng/mL or below, most preferred 0.01 ng/mL or below; and
(iii) determining whether said patient has a bacterial infection or not by comparing said determined PCT level with a predetermined threshold level.

The invention further relates to the use of such a method for providing treatment guidance for the administration of an antibiotic to a patient who has suffered from an acute stroke or from a transient ischemic attack and for monitoring the antibiotic therapy.

Due to the high sensitivity of PCT level detection, the invention allows for the earlier detection of bacterial infections and subsequently an earlier treatment of said bacterial infections in a patient who has suffered from an acute stroke or from a transient ischemic attack and therefore for the improvement of the patient outcome. Therefore, the method is particularly suitable to be applied with samples from patients who are in intensive care in a medical institution, such as a hospital. One should have in mind that even a 5% absolute improvement in favourable outcome due to an early identification and early antibiotic treatment of a bacterial infection is worthwhile as even a small outcome improvement would have major public-health implications (Lees et al. 2003. Lancet Neurology 2: 54-61). Thus, the early treatment of patients in need is of great importance.

DETAILED DESCRIPTION OF THE INVENTION

The present invention relates to a method, in particular to an in vitro method for diagnosing or identifying a bacterial infection in a patient who has suffered from an acute stroke or from a transient ischemic attack (TIA). The method comprises the following steps:
  (i) providing a sample from a patient who has suffered from an acute stroke or a transient ischemic attack;
  (ii) determining the level of Procalcitonin (PCT) or a fragment thereof of at least 12 amino acids in length, preferably more than 50 amino acids in length, more preferably more than 110 amino acids in length, in said sample using a PCT detection assay with a functional assay sensitivity of below 0.06 ng/mL, more preferred 0.04 ng/mL or below, even more preferred 0.03 ng/mL or below, most preferred 0.01 ng/mL or below; and
  (iii) determining whether said patient has a bacterial infection or not by comparing said determined PCT level with a predetermined threshold level.

The functional assay sensitivity of the PCT detection assay is preferably below 0.06 ng/ml, more preferably 0.04 ng/mL or below, even more preferred 0.03 ng/mL or below, most preferred 0.01 ng/mL or below. The Functional assay sensitivity (FAS) is defined as the lowest concentration of an assay that can be measured with an interassay coefficient of variance (CV) of 20% (Spencer C A. 1989. J Clin Immunoassay 12: 82-9). Such a low functional assay sensitivity allows for the correlation of PCT levels after acute stoke or TIA with the likelihood of a bacterial infection developing in a patient a few days after suffering from the stroke or TIA.

The majority of post-stroke infections are acquired post-stroke and appear within 7 days post-stroke. Thus, the present invention is especially useful in diagnosing or identifying a bacterial infection that has been acquired post-stroke. This means the method is especially useful for post-stroke patients which did not have an infection before stroke. Post-stroke acquired infections may occur as a result of stroke-treatment, the use of invasive medical procedures (e.g. aspiration due to drowsiness, impaired bulbar reflexes and dysphagia, catheterization in immobilized patients (Perry and Love 2001. Dysphagia 16: 7-18). Strokes are accompanied in 10-22% by development of pneumonia within the first 7 days. Indredavik et al. 2008 shows that the infection rate of post-stroke patients may further increase up to 12 weeks post-stroke (Indredavik et al. 2008. Stroke 39: 414-20). The use of the ultrasensitive PCT assay which has a functional assay sensitivity of below 0.06 ng/ml, enables the identification of an infection at a very early time point and thus, enables an early antibiotic treatment. As a consequence the outcome and functional outcome may be considered improved diagnosing and monitoring post-stroke patients early using an ultrasensitive PCT assay.

Thus, monitoring is recommended up to 7 days, preferably up to 12 weeks, more preferably up to 6 months, more preferably up to 1 year.

In one embodiment of the invention the bacterial infection is asymptomatic (e.g. a bacterial infection that has not yet shown clinical symptoms) in a patient who has suffered from an acute stroke or from a transient ischemic attack (TIA).

The term "level" in the context of the present invention relates to the concentration (preferably expressed as weight/volume; w/v) of PCT (or a fragment/precursor) in a sample taken from a subject.

The term "patient" as used herein refers to a living human or non-human organism that is receiving medical care or that should receive medical care due to a disease. This includes persons with no defined illness who are being investigated for signs of pathology. Thus, the methods and assays described herein are applicable to both human and veterinary disease.

Preferably, the sample was taken from the patient earlier than 72 hours after the onset of acute stroke or TIA symptoms. Further, it is preferred that the sample is taken from the patient no later than 60 hours, 48 hours, 24 hours, 18 hours, 12 hours, or 6 hours, most preferred no later than 3 hours after the onset of acute stroke or TIA symptoms. According to the method post-stroke infections including nosocomial or healthcare associated infections can be diagnosed. The term "post-stroke infection" as used herein refers to a bacterial infection occurring after the onset of acute stroke or TIA symptoms. Infections are considered nosocomial or healthcare associated if they first appear 48 hours or more after hospital admission or within 30 days after discharge as a result of treatment in a hospital or a healthcare service unit. The term "health care-associated infection" (HAI) is defined in Horan et al. (Horan et al. 2008. Am J Infect Control 36: 309-32).

Thus, subject of the invention is a method for diagnosing a bacterial infection in a patient who has suffered from an acute stroke or from a transient ischemic attack, comprising the steps of:
  (i) providing a sample from a patient who has suffered from an acute stroke or a transient ischemic attack wherein the sample was taken from said patient earlier than 72 hours after the onset of acute stroke or transient ischemic attack symptoms;
  (ii) determining the level of Procalcitonin (PCT) or a fragment thereof of at least 12 amino acids in length in said sample using a PCT detection assay with a functional assay sensitivity of below 0.06 ng/mL; and
  (iii) determining whether said patient has a bacterial infection or not by comparing said determined PCT level with a predetermined threshold level.

The term "sample" as used herein refers to a sample of bodily fluid obtained for the purpose of diagnosis, prognosis, or evaluation of a subject of interest, such as a patient. Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus in a preferred embodiment of the invention the sample is selected from the group consisting of a blood sample, a serum sample, a plasma sample, a cerebrospinal fluid sample, a saliva sample and an urine sample or an extract of any of the aforementioned samples. Preferably, the sample is a blood sample, most preferably a serum sample or a plasma sample.

The term acute stroke as used herein refers to both an ischemic and a hemorrhagic stroke.

As mentioned herein in the context of proteins or peptides, the term "fragment" refers to smaller proteins or peptides derivable from larger proteins or peptides, which hence comprise a partial sequence of the larger protein or peptide. Said fragments are derivable from the larger proteins or peptides by saponification of one or more of its peptide bonds.

Procalcitonin in the context of the present invention preferably relates to a peptide spanning amino acid residues 1-116, 2-116, or 3-116 or fragments thereof. Thus the length of procalcitonin fragments is at least 12 amino acids, preferably more than 50 amino acids, more preferably more than 110 amino acids. PCT may comprise posttranslational modifications such as glycosylation, liposidation or derivatisation. PCT itself is a precursor of calcitonin and katacalcin. The amino acid sequence of PCT 1-116 is given in SEQ ID NO:1.

According to the method, the patient is diagnosed with having a latent bacterial infection when said determined PCT level is higher than the predetermined threshold level. Preferably, the predetermined threshold level is between 0.02 and 0.5 ng/mL, more preferably between 0.02 ng/mL and 0.25 ng/mL, even more preferred between 0.02 ng/mL and 0.1 ng/mL, even more preferred between 0.02 ng/mL and 0.06 ng/mL, most preferred between 0.02 ng/mL and (below) 0.05 ng/mL.

Determining the level of PCT or a fragment or a precursor or fragment thereof herein is performed using a detection method and/or a diagnostic assay.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$.

In the context of the present invention, "capture molecules" are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a RNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13: 978-0080445267; Hultschig C et al., Curr Opin Chem. Biol. 2006 February; 10(1):4-10. PMID: 16376134, incorporated herein by reference).

In a particularly preferred embodiment the assay comprises two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, auch as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethody-fluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like. In the context of the present invention, chemiluminescence based assays comprise the use of dyes, based on the physical principles described for chemiluminescent materials in Kirk-Othmer, Encyclopedia of chemical technology, 4th ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

It is most preferred to use commercially available PCT test systems with a functional assay sensitivity of 0.007 ng/mL as described in Morgenthaler et al. (Morgenthaler et al. 2002. Clin Chem 48:788-790) in the method of the invention.

The bacterial infection that might be diagnosed with the method of the invention can be treated with a suitable antibiotic, as known to a person of skill in the art. Possible classes of antibiotics are selected from the group consisting of penicillin (e.g. flucloxacillin, amoxicillin, ampicillin, mezlocillin), cephalosporin (e.g. cefazolin, cefuroxim, cefotaxim, cefaclor, cefalexin), β-lactamase inhibitor (e.g. sulbactam, tazobactam), tetracycline (e.g. doxycyclin, minocyclin, tetracyclin, oxytetracyclin), aminoglycoside (e.g. gentamicin, neomycin, streptomycin), makrolid antibiotics (e.g. azithromycin, clarithromycin, erythromycin, roxithromycin, spiramycin, clindamycin), lincosamide (e.g. lincomycin), gyrase inhibitor (e.g. ciprofloxacin, ofloxacin, norfloxacin), sulfonamides, trimethoprim, glycopeptide antibiotics (e.g. vancomycin), polypeptide antibiotics (e.g. colistin, polymyxin), and amphenicole (e.g. chloramphenicol).

The method of the invention may further comprise the step of administering an antibiotic to the patient before the patient shows clinical symptoms of a bacterial infection.

The method is particularly suitable when the bacterial infection is a respiratory tract infection including pneumonia and tracheobronchitis, a urinary tract infection or a sepsis. As known to a person of skill in the art, pneumonias can be caused by a range of different organisms. It is therefore preferred to use a broad band antibiotic to be administered to the patient to prevent the bacterial infection from showing clinical symptoms chloramphenicol, tetracycline, streptomycin, amoxycillin, levofloxacin, gatifloxacin, moxifloxacin Further markers may be determined to diagnose or identify an asymptomatic bacterial infection. These markers can be selected from the group consisting of: C-reactive protein (CRP), neopterin, count of white blood cell (WBC), body temperature, neutrophils, erythrocyte sedimentation rate (ESR).

In a further aspect, the invention refers to the use of the described method for providing treatment guidance for the administration of an antibiotic to a patient who has suffered from an acute stroke or from a transient ischemic attack.

In a further aspect, the invention refers to the use of the described method for preventive treatment of a patient who has suffered from an acute stroke or from a transient ischemic attack with an antibiotic.

Furthermore, the invention pertains to the use of a kit comprising one or more antibodies directed against PCT or a fragment thereof or against a PCT precursor or fragment thereof for the diagnosis of a post-stroke bacterial infection in patients having suffered an acute ischemic or hemorrhagic stroke or TIA.

BRIEF DESCRIPTION OF THE DRAWINGS

Figures

EXAMPLES

Example 1

Clinical Study Description

Figure 1:
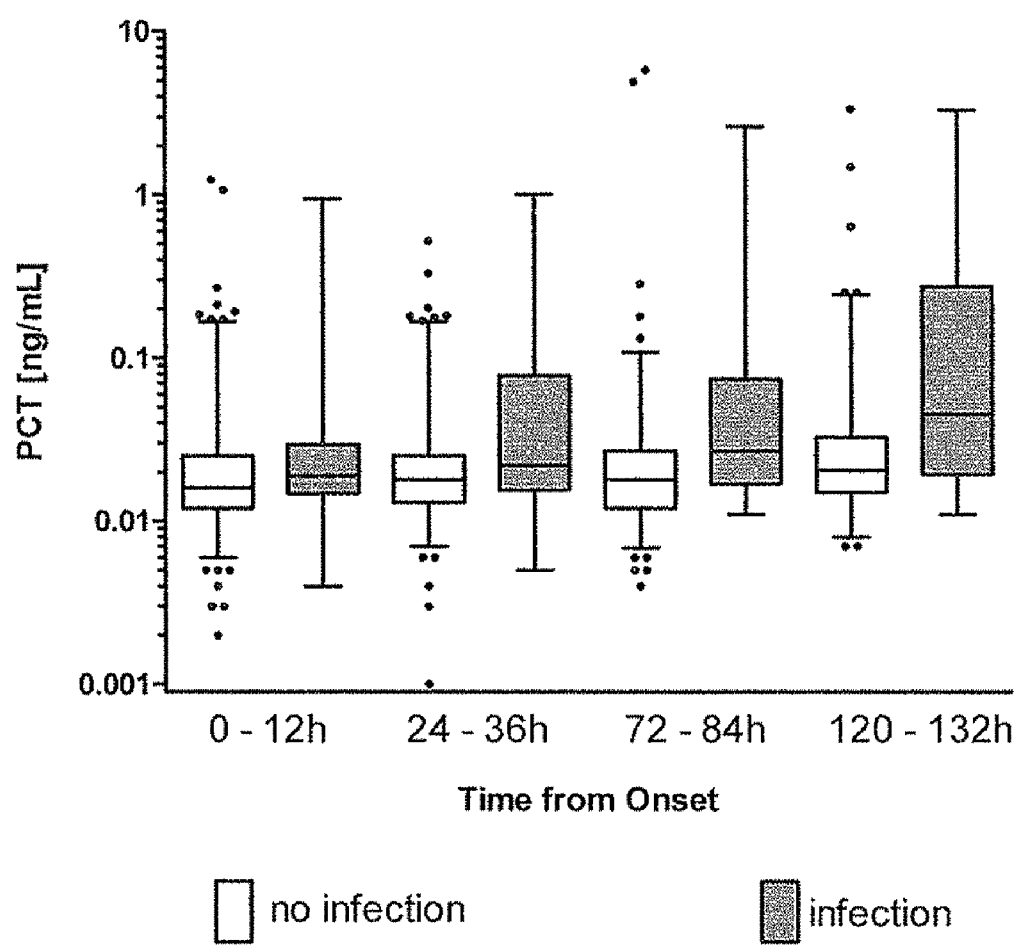
FIG. 1: Shows PCT concentrations over time in acute stroke and TIA patients (admitted to the hospital and first blood draw within 12 hours after onset of acute stroke or TIA symptoms) with and without infection

The study was set at the emergency and neurological and neurosurgical clinic of the University Hospital of Basel. All consecutive patients who are admitted to the emergency department with an ischemic or hemorrhagic stroke or transient ischemic attack (TIA) according to the World Health Organization criteria with symptom onset within the last 3 days were included into the study. Patients without an informed consent were excluded. Baseline data collection in patients contained:

a) age,
b) gender,
c) body mass index (BMJ),
d) medical history items: actual history that preceded the hospitalization; ABCD score (Rothwell et al. 2005. Lancet 366: 29-36) in patients with transient ischemic attack; family history; relevant co-morbidities also assessed by the charlson index (Goldstein et al. 2004. Stroke 35: 1941-5) (i.e. hypertension, previous stroke, previous TIA, ischemic heart disease, atrial fibrillation, diabetes mellitus, renal and liver dysfunction, congestive heart failure, dyslipidemia; comorbidities with the risk of hyponatremia (severe hypothyroidism, glucocorticoid insufficiency, neoplasm, HIV infection); smoking history (pack-years) and status (pack per day); current medication; alcohol consumption (glass and grams per day); time from onset of symptoms to admission.
e) Place of residence: i.e. independent living, defined as living at home or in an old people's home with or without support of the family circle and/or professional care (the family circle consists of the spouse and/or other important persons who live together with the patient; dependent living, defined as nursing home long-stay department, other hospital.
f) Clinical items: physical examination including neurological status, NIHSS (to assess the severity of stroke) and Glasgow Coma scale (GCS; Adams et al. 1999. Neurology 53: 126-31), blood pressure, pulse rate, weight, volume status (including skin turgor, jugular venous distension, auscultation, if available flow sheet of fluid intake and loss), body temperature; in neurosurgical patients intracerebral pressure if performed within the routine clinical management.
g) Clinical symptoms of hyponatraemia were evaluated on admission and in case of sodium imbalance in neurological patients. In patients undergoing intracranial surgery we will evaluate clinical symptoms daily. Specifically, we monitored the presence of headache, anorexia, nausea, vomiting, muscle cramps and aches, seizures, confusion, apathetic or lethargic development.
h) Routine/Standard laboratory tests: routine blood sampling including: hematocrit, blood urea nitrogen, bicarbonate, total protein, albumin, uric acid serum and urine electrolytes, urine and serum osmolality, creatinine, lipids, TSH, fT4, T3, and basal cortisol. AU blood sampling was done before any food intake, or smoking, if feasible. Alternatively, influencing factors were monitored.
i) Imaging: Computer tomography or MRI of the neurocranium (T1, T2, diffusion-weighted image sequence, with or without contrast), if indicated magnetic resonance angiography or conventional cerebral angiography. We recorded the time-points of contrast agent application. Stroke, patients will also be classified on the basis of the vascular territory of the ischemic lesion as follows: total anterior circulation syndrome (TACS), partial anterior circulation syndrome (PACS), lacunar circulation syndrome (LACS), posterior circulation syndrome (POCS).
j) Further investigations: Stroke patients had neurosonography, echocardiography, standard 12-leaf electrocardiography and 24-hour electrocardiography and were then classified by etiology of strokes according to Trial of Org 10172 in acute Treatment (TOAST) stroke subtype classification, which differs between large artery atherosclerosis, cardioembolism, small-artery occlusion, other etiology, and undetermined etiology.

The study was be approved by the ethics committee of Basel (Ethikkommission beider Basel). This was an exploratory and observational study; the only study related intervention was the asseveration of 7.5 ml of plasma obtained during the routinely performed blood sampling. Therefore, patients provided a written informed consent that they agree for the use of their data for scientific purposes. In patients, in which "informed consent" was not feasible due to sequela of the acute CNS lesion (the latter a prerequisite for inclusion), patients' next to kin signed an assent form to state the presumptive will of the patient. In case, next of kin were not readily available, a treating physician—who was not be involved in the study—certified that there were no objections for inclusion in the study from his point of view. Only after these informed consent procedures the patient was included in the study.

Management of Participants Throughout the Trial:

Step 1. All eligible patients in the emergency department or the neurological ward were included into the study.

Step 2. All baseline data were collected.

Step 3. During hospitalization the clinical items including weight, blood pressure, pulse rate, volume status and body temperature were assessed by chart review until discharge.

fluid treatment and drugs potential symptoms of hyponatremia, i.e. headache, nausea, vomiting, muscle cramps and aches, anorexia, impaired consciousness, seizure.

routinely performed laboratory tests (chemogramm, plasma glucose, serum osmolality, urine osmolality, sodium in urine, hematocrit) were sampled at the timepoints when blood sampling is routinely done on the wards.

Step 4. In all patients, on day 5 of the hospitalization, a clinical examination with NIHSS, Barthel Index and Ranking Scale was performed (Collin et al. 1988. International Disability Study 10: 61-3; Bonita and Beaglehole. 1988. Stroke 19: 1497-1500). The future place of residence (i.e. dependent vs. independent living) was assessed.

Step 5. In patients with ischemic stroke a telephone follow-up regarding morbidity and mortality (as assessed by the Barthel Index and Ranking Scale) was obtained after 3 months. An unfavorable outcome was defined as a Barthel index<85 or modified Ranking scale of 3 to 6.

Example 2

Measurement of Procalcitonin

PCT was measured using an ultrasensitive commercially available test system with a functional assay sensitivity of 0.007 ng/mL as described in Morgenthaler et al. (Morgenthaler et al. 2002. Clin Chem 48:788-790). Briefly, sheep antibodies were raised against the calcitonin moiety of PCT, and a mouse monoclonal antibody was raised against the katacalcin moiety of PCT. Tubes were coated with the anti-katacalcin antibody. The anti-Calcitonin antibody was labelled with MACN Acridiniumester (InVent GmbH, Hennigsdorf, Germany) and served as tracer. Dilutions of recombinant PCT in normal horse serum were used as calibrators. 100 µl, sample or standard was incubated in the coated tubes for 30 minutes, 200 µL tracer was added. After further incubation for 2 h the tubes were washed 4 times with 1 mL of LIA wash solution (BRAHMS A G, Hennigsdorf, Germany), and bound chemiluminescence was measured using a LB952T luminometer (Berthold, Wildbad, Germany).

Results

The level of procalcitonin was determined in blood samples of patients having diagnosed to suffer from a stroke (either ischemic or hemorrhagic) or a transient ischemic attack. In a first approach patients were included into the analysis when they were admitted to the hospital within the first 12 hours after onset of acute stroke or TIA symptoms (n=376). Concentrations of procalcitonin were determined at baseline (on admission to the hospital) and on day 1 (24-36 h), 3 (72-84 h) and 5 (120-132 h) after admission. 24 out of these 376 patients developed a bacterial infection (e.g. pneumonia, urinary tract infection) after stroke/TIA onset. PCT concentrations over time for patients (admitted to the hospital within 12 hours after onset of acute stroke and TIA symptoms) with and without a bacterial infection are shown in FIG. 1. Logistic regression analysis revealed an association between increased PCT concentration and presence of bacterial infection ($p=0.12$ on admission (0-12 h); $p=0.067$ on day 1 (24-36 h); $p=0.0042$ on day 3 (72-84 h) and $p=0.011$ on day 5 (120-132 h). Different cut-off values were used to determine the corresponding sensitivity and specificity (Table 1). At a PCT cut-off value of 0.06 ng/mL sensitivity and specificity on admission of the patient within 12 hours after the onset of acute stroke/TIA symptoms were 9.1 and 94.1%, respectively. If this cut-off value is bisected to 0.03 ng/mL, sensitivity more than doubled (22.7%) with a moderate decline in specificity (85.7%). If PCT was measured within 24 to 36 hours after symptom onset sensitivity and specificity were 28.2 and 94.6%, respectively, at a PCT cut-off of 0.06 ng/mL, whereas at a PCT cut-off value of 0.03 ng/mL sensitivity increased up to 33.3% at a specificity of 82.9%.

Figure 2:
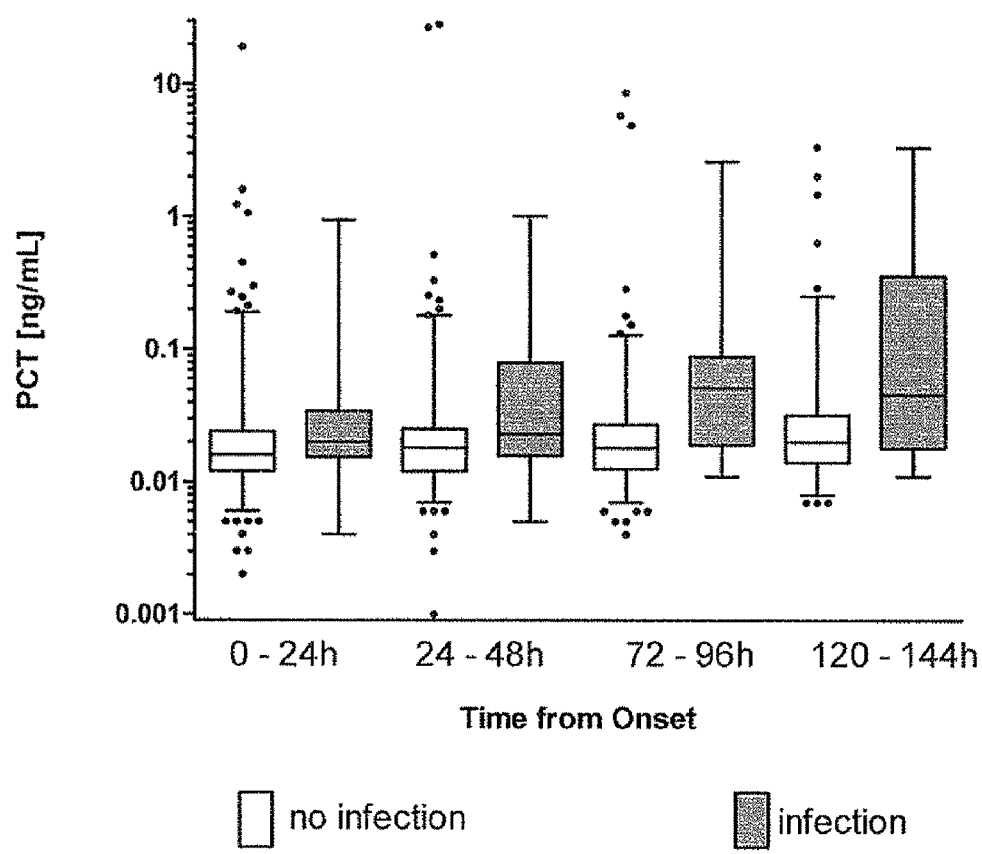
FIG. 2: Shows PCT concentrations over time in acute stroke and TIA patients (admitted to the hospital and first blood draw within 24 hours after onset of acute stroke or TIA symptoms) with and without infection

In a second approach patients were included into the analysis when they were admitted to the hospital within the first 24 hours after onset of symptoms (n=432). Concentrations of procalcitonin were determined at baseline (on admission to the hospital) and on day 1 (24-48 h), 3 (72-96 h) and 5 (120-144 h) after admission. 26 out of these 432 patients developed a bacterial infection (e.g. pneumonia, urinary tract infection) after stroke/TIA onset. PCT concentrations over time for patients with and without a bacterial infection are shown in FIG. 2. Logistic regression analysis revealed an association between increased PCT concentration and presence of bacterial infection ($p=0.035$ on admission (0-24 h); $p=0.029$ on day 1 (24-48 h); $p=0.0005$ on day 3 (72-96 h) and $p=0.01$ on day 5 (120-144 h). Different cut-off values were used to determine the corresponding sensitivity and specificity (Table 2). At a PCT cut-off value of 0.06 ng/mL sensitivity and specificity on admission of the patient within 24 hours after the onset of acute stroke/TIA symptoms were 16.7 and 94.4%, respectively. If this cut-off value is bisected to 0.03 ng/mL, sensitivity almost doubled (29.2%) with a moderate decline in specificity (85.3%). If PCT was measured within 24 to 48 hours after symptom onset sensitivity and specificity were 31.8 and 93.5%, respectively, at a PCT cut-off of 0.06 ng/mL, whereas at a PCT cut-off value of 0.03 ng/mL sensitivity increased up to 40.9% at a specificity of 81.5%.

To consider the high quality of Procalcitonin it has to be taken into account that the diagnosis of post-stroke infections in this study was carried out according to standard criteria: temperature>37.5° C., white blood cell count>11 000/mL or <4000/mL, pulmonary infiltrate on chest x-rays, or cultures positive for a pathogen. This gold standard diagnosis of infection underestimates the true number of infections to a great extent, resulting in a rather high number of false negatives (meaning that acute stroke or TIA patients with an actual bacterial infection may be falsely allocated to the non-infectious subgroup). With the test system described in the present invention for ultrasensitive detection of Procalcitonin those false negatives can be diagnosed correctly as having a bacterial infection and thus can be treated adequately with antibiotics.

Sequence

SEQ ID NO: 1 (amino acid sequence of PCT):

```
  1 APFRSALESS PADPATLSED EARLLLAALV QDYVQMKASE
    LEQEQEREGS

51 SLDSPRSKRC GNLSTCMLGT YTQDFNKFHT FPQTAIGVGA
    PGKKRDMSSD

101 LERDHRPHVS MPQNAN
```

TABLE 1

Sensitivities and Specificities (in %) for different PCT cut-off values at different measuring time points for acute stroke and TIA patients who were admitted to the hospital within 12 hours after symptom onset

| PCT-Cut off (ng/ml) | 0-12 h Sens. (%) | 0-12 h Spec. (%) | 24-36 h Sens. (%) | 24-36 h Spec. (%) | 72-84 h Sens. (%) | 72-84 h Spec. (%) | 120-132 h Sens. (%) | 120-132 h Spec. (%) |
|---|---|---|---|---|---|---|---|---|
| 0.03  | 22.7 | 85.7 | 33.3 | 82.9 | 46.7 | 81.6 | 56.3 | 71.9 |
| 0.045 | 13.6 | 92.2 | 28.6 | 91.1 | 46.7 | 89.3 | 56.3 | 84.8 |
| 0.06  | 9.1  | 94.1 | 28.2 | 94.6 | 40.0 | 92.7 | 31.3 | 93.3 |
| 0.1   | 9.1  | 96.1 | 9.5  | 96.2 | 13.3 | 97.0 | 31.3 | 96.4 |

TABLE 2

Sensitivities and Specificities (in %) for different PCT cut-off values at different measuring time points for acute stroke and TIA patients who were admitted to the hospital within 24 hours after symptom onset

| PCT Cut-off (ng/ml) | 0-24 h Sens. (%) | 0-24 h Spec. (%) | 24-48 h Sens. (%) | 24-48 h Spec. (%) | 72-96 h Sens. (%) | 72-96 h Spec. (%) | 120-144 h Sens. (%) | 120-144 h Spec. (%) |
|---|---|---|---|---|---|---|---|---|
| 0.03  | 29.2 | 85.3 | 40.9 | 81.5 | 52.9 | 81.8 | 55.6 | 72.9 |
| 0.045 | 20.8 | 91.7 | 31.8 | 90.5 | 52.9 | 89.1 | 55.6 | 85.4 |
| 0.06  | 16.7 | 94.4 | 31.8 | 93.5 | 47.1 | 92.3 | 33.3 | 92.7 |
| 0.1   | 12.5 | 96.1 | 13.7 | 95.8 | 17.7 | 96.8 | 33.3 | 96.0 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding EP application No. 09012947.9, filed Oct. 13, 2009, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for diagnosing a bacterial infection in a patient who has suffered from an acute stroke or from a transient ischemic attack, comprising the steps of:
   (i) providing a sample from a patient who has suffered from an acute stroke or a transient ischemic attack wherein the sample was taken from said patient earlier than 72 hours after the onset of acute stroke or transient ischemic attack symptoms;
   (ii) determining the level of Procalcitonin (PCT) or a fragment thereof of at least 12 amino acids in length in said sample using a PCT detection assay with a functional assay sensitivity of below 0.06 ng/mL; and
   (iii) determining whether said patient has a bacterial infection or not by comparing said determined PCT level with a predetermined threshold level.

2. The method of claim 1, wherein the sample was taken from said patient earlier than 48 hours after the onset of acute stroke or transient ischemic attack symptoms.

3. The method of claim 1, wherein said sample is a bodily fluid.

4. The method of to claim 1, wherein the acute stroke is an ischemic or a hemorrhagic stroke.

5. The method of claim 1, wherein the PCT fragment of the fragment of a PCT precursor has a length of at least 50 amino acid residues.

6. The method of claim 1, wherein the predetermined threshold level is between 0.02 ng/mL and 0.5 ng/mL.

7. The method of claim 1, wherein said patient has a bacterial infection when said determined PCT level is higher than the predetermined threshold level.

8. The method of claim 1, wherein said bacterial infection is treatable with an antibiotic.

9. The method according to claim 1, wherein said bacterial infection is a pneumonia.

10. The method according to claim 1, wherein said bacterial infection is asymptomatic (without clinical symptoms of a bacterial infection).

11. The method according to claim 1, further comprising the step of:
    (iv) administering an antibiotic to the patient.

12. The method according to claim 1, further comprising the step of:
    determining the level of at least one more marker.

13. The method of claim 1, wherein the determination of the PCT level provides treatment guidance for the administration of an antibiotic to a patient who has suffered from an acute stroke or from a transient ischemic attack.

14. The method of claim 6, wherein he predetermined threshold level is between 0.02 ng/mL and 0.25 ng/mL.

15. The method of claim 6, wherein he predetermined threshold level is between 0.02 ng/mL and 0.1 ng/mL.

16. The method of claim 6, wherein he predetermined threshold level is between 0.02 ng/mL and 0.06 ng/mL.

17. The method of claim 6, wherein he predetermined threshold level is between 0.02 ng/mL and (below) 0.05 ng/mL.

18. The method of claim 3, wherein the bodily fluid is blood, serum, plasma, cerebrospinal fluid, urine, saliva or a pleural effusion.

19. The method of claim 12, wherein the marker is C-reactive protein (CRP), neopterin, count of white blood cell (WBC), body temperature, neutrophils, erythrocyte sedimentation rate (ESR).

20. The method of claim 2, wherein the sample was taken from said patient earlier than 24 hours after the onset of acute stroke or transient ischemic attack symptoms.

21. The method of claim 2, wherein the sample was taken from said patient earlier than 12 hours after the onset of acute stroke or transient ischemic attack symptoms.

* * * * *

SEQUENCE LISTING

```
<160> NUMBER OF SEQ ID NOS: 1

<210> SEQ ID NO 1
<211> LENGTH: 116
<212> TYPE: PRT
<213> ORGANISM: Homo sapiens

<400> SEQUENCE: 1

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
        35                  40                  45

Gly Ser Ser Leu Asp Ser Pro Arg Ser Lys Arg Cys Gly Asn Leu Ser
    50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
            100                 105                 110

Gln Asn Ala Asn
        115
```